(12) United States Patent
Liu et al.

(10) Patent No.: US 9,017,657 B2
(45) Date of Patent: Apr. 28, 2015

(54) ISLET CELL CLUSTER PRODUCED FROM HUMAN UMBILICAL CORD MESENCHYMAL STEM CELLS

(75) Inventors: Shing-Hwa Liu, Taipei (TW); Kuo-Ching Chao, Taipei (TW); Kuo-Fang Chao, Taipei (TW)

(73) Assignee: National Taiwan University, Taipei (TW)

( * ) Notice: Subject to any disclaimer, the term of this patent is extended or adjusted under 35 U.S.C. 154(b) by 1384 days.

(21) Appl. No.: 12/320,026

(22) Filed: Jan. 15, 2009

(65) Prior Publication Data
US 2010/0015103 A1 Jan. 21, 2010

(30) Foreign Application Priority Data
Jul. 16, 2008 (TW) .............................. 097127044 A

(51) Int. Cl.
*A61K 48/00* (2006.01)
*A61K 38/27* (2006.01)

(52) U.S. Cl.
CPC ...................................... *A61K 38/27* (2013.01)

(58) Field of Classification Search
CPC A61K 38/27; A61K 2121/00; A61K 2123/00
See application file for complete search history.

(56) References Cited

U.S. PATENT DOCUMENTS

2006/0281174 A1* 12/2006 Xu et al. ...................... 435/325

OTHER PUBLICATIONS

Zhang et al (Cell Biology International, 29: 213-219, 2005).*
Lu et al (Haematologia, 91: 1017-1026, 2006).*
Murdoch et al (Cell Transplantation, 13: 605-617, 2004).*
Gao et al (Translational Research, 151: 293-302, Epub Apr. 28, 2008).*
Wang et al (Stem Cells, 22: 1330-1337, 2004).*
Liu et al, (J Biotechnol, 124: 592-601, 2006).*
Chao et al, Kuo Ching, Islet-Like Clusters Derived from Mesenchymal Stem Cells in Wharton's Jelly of the Human Umbilical Cord for Transplantation to Control Type 1 Diabetes, PLoS One, Jan. 2008, pp. 1-9, Issue 1.

* cited by examiner

*Primary Examiner* — Deborah Crouch
*Assistant Examiner* — Magdalene Sgagias
(74) *Attorney, Agent, or Firm* — Bacon & Thomas, PLLC

(57) ABSTRACT

The invention relates to a cell culture method, particularly to a co-culture method for human mesenchymal stem cells and target animal cells, in order to solve the problem that animal cells are not easy to survive alone upon culturing. The invention also provides a method for using a stem cell conditioned medium to culture animal cells. The invention also provides a method to induce the transformation of human fetal islet-like cell clusters from human stem cells and its application thereof.

7 Claims, 8 Drawing Sheets

ISLET CELL CLUSTER PRODUCED FROM HUMAN UMBILICAL CORD MESENCHYMAL STEM CELLS

BACKGROUND OF THE INVENTION

1. Field of the Invention

The invention relates to a cell culture method, particularly to a co-culture method for human mesenchymal stem cells and target animal cells.

2. Description of the Prior Art

Type I diabetes (also called insulin relied type diabetes) is mainly caused by the abnormality of pancreatic islet cell which is responsible for secreting the insulin. Though it only accounts for 5-10% of all cases of diabetes, the patients become dependent on daily injection of insulin in order to control the illness condition for life, which will influence the life of patients seriously. So, there are a lot of researches on type I diabetes.

It is generally acknowledged that islet-like cell clusters (ICCs) can generate insulin. Transplantation of islet-like cell clusters is the best method to cure type I diabetes at present. But because the supply of ICCs transplantation is insufficient, the ICCs are lost during separation and purification process, it is difficult to get enough mass purified ICCs, which is often one of the reasons to fail for the fail of ICCs transplantation. In addition, ex vivo culture of ICCs is very difficult, and the common culture method cannot exceed 3 to 5 days. Even the worldwide famous Edmonton method (the operation of transplanting ICCs donated by the dead person to diabetes patient) shall transplant ICCs to the diabetes patient within 2 hours. Because in the present common ex vivo culture method, ICCs will be denatured, dead, and unable to be utilized Therefore, due to the difficulty for culturing ICCs, the present invention proposes a cell culture method and application thereof. The invention is described briefly as follows.

SUMMARY OF THE INVENTION

The present invention provides a cell culture method, particularly to a co-culture method for human mesenchymal stem cells and target animal cells, in order to solve the problem that animal cells are not easy to survive alone upon culturing. The activity and function of target animal cells can be maintained. The present invention also provides a method for using a stem cell conditioned medium to culture animal cells. Finally, the present invention also provides a method to induce the transformation of human islet-like cell clusters from human stem cells and application thereof.

One aspect of the present invention is to provide a cell culture method, which includes the steps of preparing a suspended medium containing human stem cells, adding target animal cells to be cultured, and co-culturing the target cells at a suitable condition.

According to one embodiment of the present invention, the human stem cells are human mesenchymal stem cells.

According to a preferred embodiment of the present invention, the target animal cells are mammalian cells.

Preferably, the mammalian cells are human cells.

More preferably, the human cells are islet-like cell clusters.

According to another embodiment of the present invention, the human stem cells and the target animal cells are sequentially inoculated to culture plates.

According to another embodiment of the present invention, after the human stem cells and target animal cells are inoculated for certain time, the culture medium is used to wash off the non-adherent cells from culture plates.

Another aspect of the present invention is to provide a cell culture method, which includes the steps of preparing a stem cell conditioned medium, adding target animal cells to be cultured, and culturing the target cells at a suitable condition, wherein the stem cell conditioned medium is composed of basic culture medium and a active component.

According to an embodiment of the present invention, one or more active components are selected from the group consisting of interleukin-6 (IL-6), tissue inhibitor of metalloproteinase-1 (TIMP-1), tissue inhibitor of metalloproteinase-2 (TIMP-2), monocyte chemoattractant protein-1 (MCP-1), growth related oncogene (GRO), hepatocyte growth factor (HGF), insulin-like growth factor binding protein 4 (IGFBP-4) and interleukin-8 (IL-8).

According to a preferred embodiment of the present invention, the target animal cells are mammalian cells.

Preferably, the mammalian cells are human cells.

More preferably, the human cells are islet-like cell clusters.

Another aspect of the present invention is to provide a method of inducing human stem cells differentiate into human islet-like cell clusters, which includes the steps of separating human stem cells, culturing human stem cells in a neuronal conditioned medium, and culturing the human stem cells in a first conditioned medium and a second conditioned medium sequentially.

According to one embodiment of the present invention, the neuronal conditioned medium is the cell medium for culturing mammalian brain cells.

According to another embodiment of the present invention, the first conditioned medium includes DMEM/F12 medium, glucose, insulin, nicotinamide, and B27.

Preferably, the concentration of glucose is 20 to 30 mM.

More preferably, the concentration of glucose is 25 mM.

According to a preferred embodiment of the present invention, the first conditioned medium further includes 2% fetal bovine serum.

According to another preferred embodiment of the present invention, the second conditioned medium is prepared by adding the stem cell conditioned medium into the first conditioned medium.

According to another embodiment of the invention, the human stem cells are human mesenchymal stem cells.

Another aspect of the present invention is to provide a method of using the islet-like cell clusters prepared according to the present invention to inhibit type I diabetes, which includes the steps of transplanting the human islet-like cell clusters to the liver of a subject in need thereof.

During primary culture or before a preparation of transplantation, many kinds of cell cannot survive very long ex vivo. The cell culture method of the present invention uses co-culture of human umbilical cord mesenchymal stem cells (HUMSCs) or stem cell conditioned medium to overcome the above-mentioned problem, to make target cells survive longer, and to maintain the function of the cells. After the cells are cultured according to the cell culture method of the present invention, the abnormal growth of cells or generation of cancer cells will not be occurred.

The embryonic stem cells need a special culture environment to growth ex vivo. For example, they need leukemia inhibitor factor (LIF) to promote the proliferation of stem cells and inhibit the differentiation of stem cells. Because the human umbilical cord mensenchymal stem cells (HUMSCs) do not need special environment to growth ex vivo, they are easier to be cultured compared to the embryonic stem cells. Therefore, the present invention employs HUMSCs to co-culture with other target cells, in order to maintain the survival and function of co-cultured target cells. When HUMSCs are used for co-culture, the cell clusters can be protected from damage. Consequently, it can be used as a novel cell culture. Before the transplantation or experiment of target cell clusters, it can be used to increase the number of target cells, and maintain the survival and function of target cells.

HUMSCs are isolated from the human umbilical cord, which can be easily obtained and processed compared to embryonic and bone marrow stem cells, and can be cultured without the utilization of special hormone. HUMSCs possess excellent self-renewing, repair and proliferative capabilities. As for the culture of HUMSCs, the category and concentration of secreted hormone are easy to be controlled and verified, so it is easy to carry on the assessment of scientific experiment. In addition, the safety is very high, so long as the mother and infant are healthy, there will be no infection problem for HUMSCs, which can be used for mass production, and it is not necessary to check whether it is infected by virus again.

According to the cell culture method of the present invention, the co-culture of HUMSCs can maintain the survival and function of target cells. As exampled by the culture of rat islet-like cell clusters, when the rat ICCs are co-cultured with HUMSCs, the number of rat ICCs and secretion amount of insulin can be increased for 3 months continuously. However, the rat ICCs which do not co-culture with HUMSCs will be damaged gradually and died within 12 days.

According to the cell culture method of the present invention, the cells used for co-culture with HUMSCs include but not limited to ICCs or kidney cells.

In addition, according to the cell culture method of the present invention, when the stem cell conditioned medium is used to culture target cells, the effect is equivalent to the result of using HUMSCs for co-culture. The active ingredients in stem cell conditioned medium (SCM) is similar to the active ingredients in co-culture medium, including the interleukin-6 (IL-6), tissue inhibitor of metalloproteinase-1 (TIMP-1), tissue inhibitor of metalloproteinase-2 (TIMP-2), monocyte chemoattractant protein-1 (MCP-1), growth related oncogene (GRO), hepatocyte growth factor (HGF), insulin-like growth factor binding protein 4 (IGFBP-4) and interleukin-8 (IL-8). For example, if the stem cell conditioned medium is used to transform stem cells into ICCs, it can maintain the survival and function of ICCs for more than 2 weeks, and still possesses the insulin secretion capability. It can be said that the culture by the stem cell medium has the same effect with respect to the co-culture of HUMSCs. The transformed ICCs still possesses the insulin secretion capability, so they can be transplanted to the liver of a subject in need thereof, and applied to inhibit type I diabetes further.

Summarized by the above-mentioned description, according to the cell culture method of the present invention, the co-culture of HUMSCs or the stem cell conditioned medium can be used to culture, promote or maintain the survival and function of target cells, and promote or maintain renewing, repair and proliferative capabilities of target cells.

DESCRIPTION OF THE PREFERRED EMBODIMENT

The cell culture method and its application provided by the present invention can be fully understood by the description of the following embodiments, and can be readily made by those skilled in the art, but the execution type of the present invention is not limited to the following embodiments.

Embodiment 1:Preparation of HUMSCs

With the consent of the parents, fresh human umbilical cords were obtained after birth and collected in HBSS buffer solution (Gibco) at 4° C. HUMSCs were obtained as previously described by Hu et al. (Conversion of human umbilical cord mesenchymal stem cells in Wharton's jelly to dopaminergic neurons in vitro: Potential therapeutic application for parkinsonism. Stem Cells 24:115-124; 2006). Briefly, the mesenchymal tissue of Wharton's jelly of the umbilical cord was diced into cubes of about 0.5 cm$^3$ and centrifuged at 250×g for 5 minutes; and then the mesenchymal tissue was treated with collagenase type I (Sigma) at 37° C. for 18 hours, washed and further digested with 2.5% trypsin (Gibco) at 37° C. for 30 minutes. The digested mixture was then passed through a 100 μm filter to obtain cell suspensions. Then the cell suspensions were centrifuged at 250×g for 5 minutes. The HUMSCs culture medium consisted of Dulbecco's modified Eagle's medium/F12 (DMEM/F12, 25 mM glucose, Invitrogen), 2% fetal bovine serum (Invitrogen), 1 mM glutamine, and 10 mM nicotinamide.

Embodiment 2:Preparation of Co-Culture System

Seven-day postnatal Sprague-Dawley rats were used for preparation of pancreatic cells and ICCs formation. The study was approved by The Animal Research Committee of The College of Medicine, National Taiwan University. After rats were sacrificed, pancreases were removed and cut into small pieces, and then incubated in 2 ml medium supplemented with 3 mg collagenase for 20 min at 37° C. Re-suspended to the collagenase-free medium and centrifuged at 1500 r.p.m. for 3 min. The final pellets were suspended in 12 ml DMEM/F12, 2% fetal bovine serum, 1 mM glutamine, and 10 mM nicotinamide. For preparation of co-culture system, HUMSCs were cultured in 6-well plates with 80% confluence at 37° C. Place the inserts into each prepared well with the membrane towards the well bottom, ensuring no air is trapped. Add 2 ml of single pancreatic cell suspensions to the interior of each insert (pore size 3.0 μm or 0.2 μm, Nunc).

During pancreatic cells culture, less than 30% of cells attached to the dish. Three days after seeding, non-adherent cells were removed by the medium change. Using medium with high glucose and low serum, the pancreatic cells were gradually formed cell clusters. The cluster number was about 7-8 clusters/well to 25-30 clusters/well from third day to ninth day, and cluster size was 272±44 μm at sixth day and 418±72 μm at ninth day.

Figure 1:
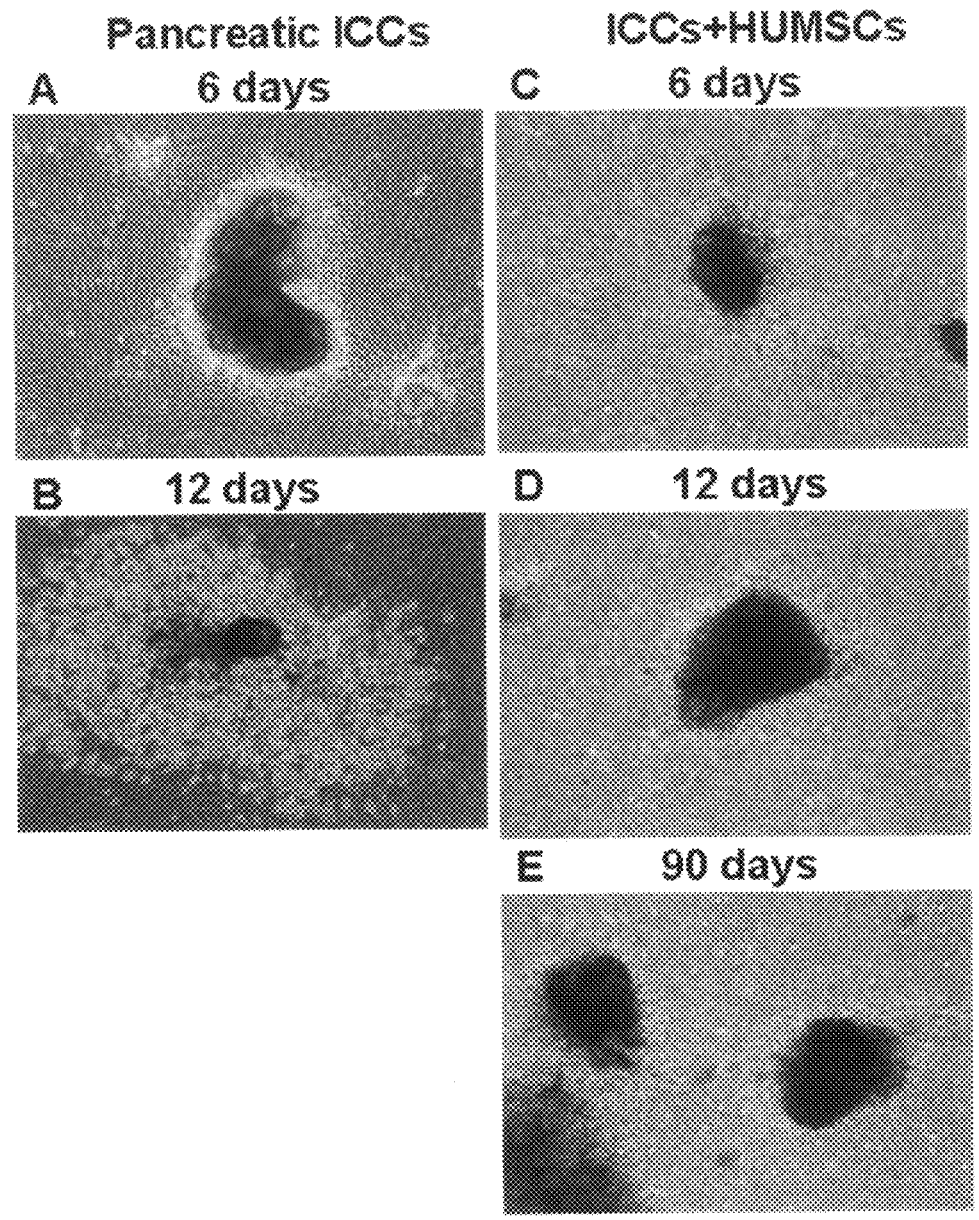
FIG. 1A, FIG. 1B, FIG. 1C, FIG. 1D, and FIG. 1E show the microscopic diagrams of pancreatic ICCs and cell clusters co-cultured with HUMSCs in accordance with the method of the present invention.

ICCs appeared on sixth day after the culture. However, after 12 days of culture, adherent cell clusters crashed, floated and died, as shown in FIG. 1A and FIG. 1B. The co-culture with HUMSCs could promote ICCs formation and survival, as shown in FIG. 1C, FIG. 1D, and FIG. 1E. The ICCs could grow and survive steadily, although the clusters numbers in ICCs/HUMSCs co-culture had not more increase than ICCs alone from day 3 to day 90. Meanwhile, HUMSCs alone did not form cell clusters.

Embodiment 3:Insulin Quantification Assay

To test whether ICCs co-cultured in embodiment 2 still have functional characteristics of islets, we will inspect whether the activity of insulin secreted by cell is normal. The supernatants of ICCs culture and ICCs/HUMSCs co-culture medium were harvested every 3 days for insulin detection using a rat insulin-ELISA-kit (enzyme linked immunosorbent assay kit, Mercodia, Sweden). After acquiring the medium, washed plate 5 times with PBS and changed medium every 3 days.

Figure 2:
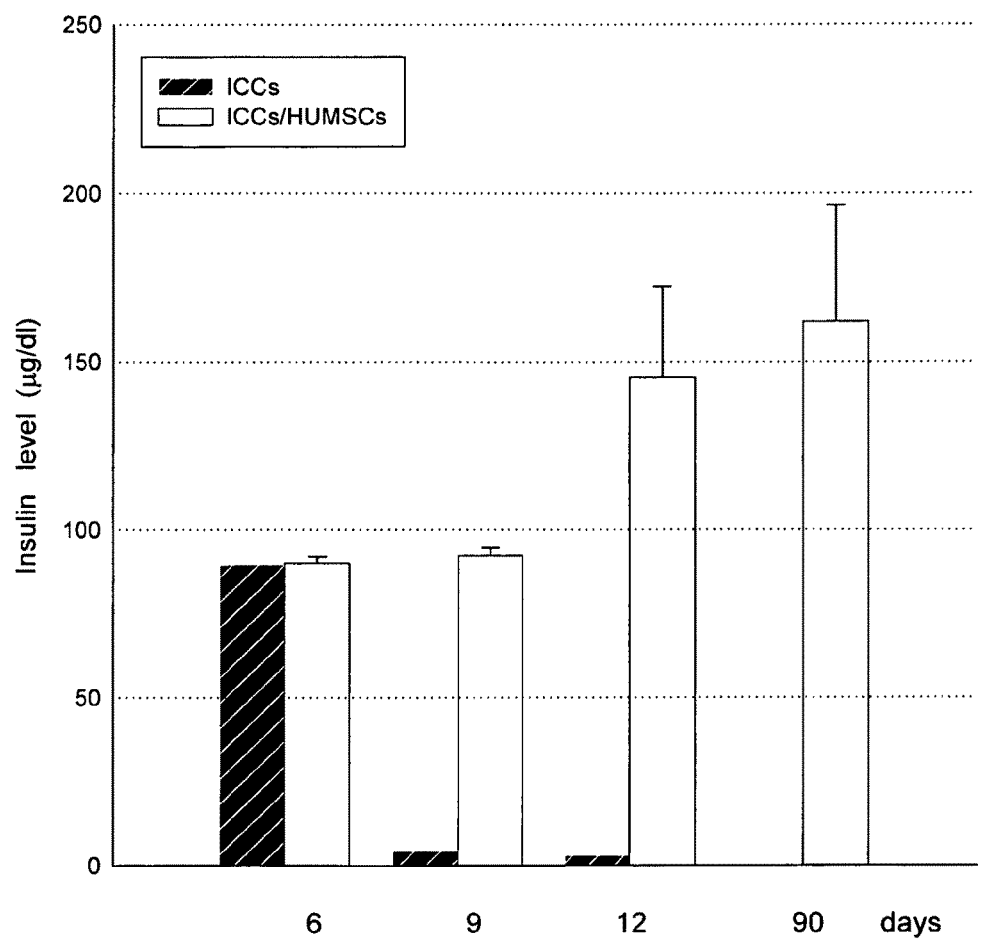
FIG. 2 shows the statistical diagram for the level of insulin secreted by cell clusters cultured in co-culture system of the present invention.

See FIG. 2, on day 6, the insulin levels of ICCs culture and ICCs/HUMSCs co-culture are 89.43±3.32 and 89.97±2.12 μg/L, respectively. However, the insulin levels in ICCs culture medium rapidly declined on day 9 (4.23±0.64 μg/L) and day 12 (2.87±0.09 μg/L). Meanwhile, the insulin levels in ICCs/HUMSCs co-culture still gradually increased on day 9 (92.35±2.18 μg/L), day 12 (145.40±26.85 μg/L), and even lasted to day 90 (160.30±31.92 μg/L). In addition, there was no human insulin detected in ICCs/HUMSCs culture medium using a specific human insulin-ELISA-kit (data not shown).

Embodiment 4:Preparation of Cytokine Test and Stem Cell Conditioned Medium

To test whether ICCs co-cultured in embodiment 2 still have other activities of islets, a human cytokine protein array was used to analyze cytokines levels in the culture medium of HUMSCs and ICCs/HUMSCs. A human cytokine protein array kit was purchased from RayBiotech (Norcross, Ga.) and used according to the manufacturer's instructions. The protein levels could be judged through fluorescence scanning.

Figure 3:
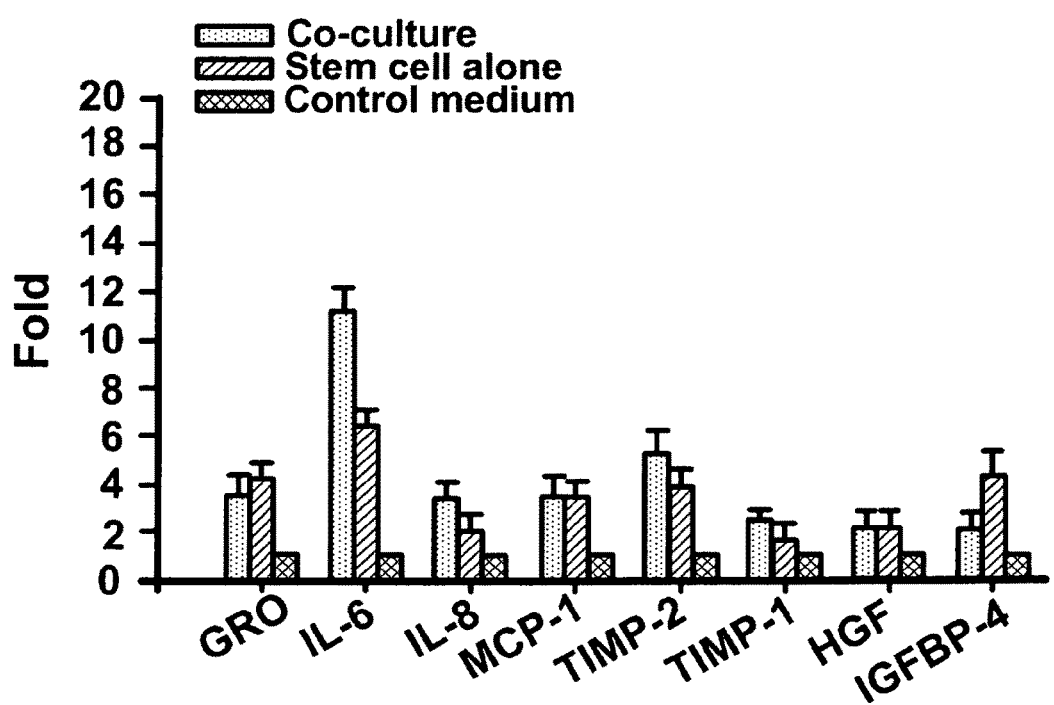
FIG. 3 shows the statistical diagram for the level of cytokine in co-culture system of the present invention.

As shown in FIG. 3, compared with non-culture medium, several cytokines levels showed more than a 2-fold increase in culture medium of ICCs/HUMSCs or HUMSCs, including interleukin-6 (IL-6), tissue inhibitor of metalloproteinases-1 (TIMP-1), tissue inhibitor of metalloproteinases-2 (TIMP-2), monocyte chemoattractant protein-1 (MCP-1), growth related oncogene (GRO), hepatocytes growth factor (HGF), insulin-like growth factor binding proteins 4 (IGFBP-4), and interleukin-8 (IL-8). It shows these cytokines secreted by HUMSCs have very important relationship for maintaining the survival and function of culture islet-like cell clusters.

Furthermore, if the above-mentioned cytokine medium (stem cell conditioned medium) is used to culture cells, it still can maintain the survival and activity of cells. It can be said that the culture by the stem cell medium has the same effect with respect to the co-culture of HUMSCs, referring to embodiment 5.

Embodiment 5:Inducement for Transformation of HUMSCs into ICCs

Firstly, a neuronal conditioned medium (NCM) was prepared by method described by Hu et al. (Conversion of human umbilical cord mesenchymal stem cells in Wharton's jelly to dopaminergic neurons in vitro: Potential therapeutic application for parkinsonism. Stem Cells 24:115-124; 2006). 10% chloride hydrate was injected into the abdominal cavity of seven-day postnatal Sprague-Dawley rats. After they were anaesthetized, the brain was excised. Suspended to the calcium/magnesium ion-free buffer solution (Gibco), and centrifuged at 900 r.p.m. for 3 min. After the supernatant was removed, DMEM medium with 10% fetal bovine serum was added to the settled substance (brain tissue). The suspended brain tissue was ground for 15 min, in order to be dispersed into the single cell. The cells were suspended in DMEM medium with 10% fetal bovine serum (FBS/DMEM), and cultured in 5% $CO_2$, 95% $O_2$ at 37□. On day 2, 2 μM of Cytarabine, Ara C (Sigma-Aldrich) was added. On day 5, the medium was harvested as the neuronal conditioned medium used for further culture of HUMSCs.

Figure 4:
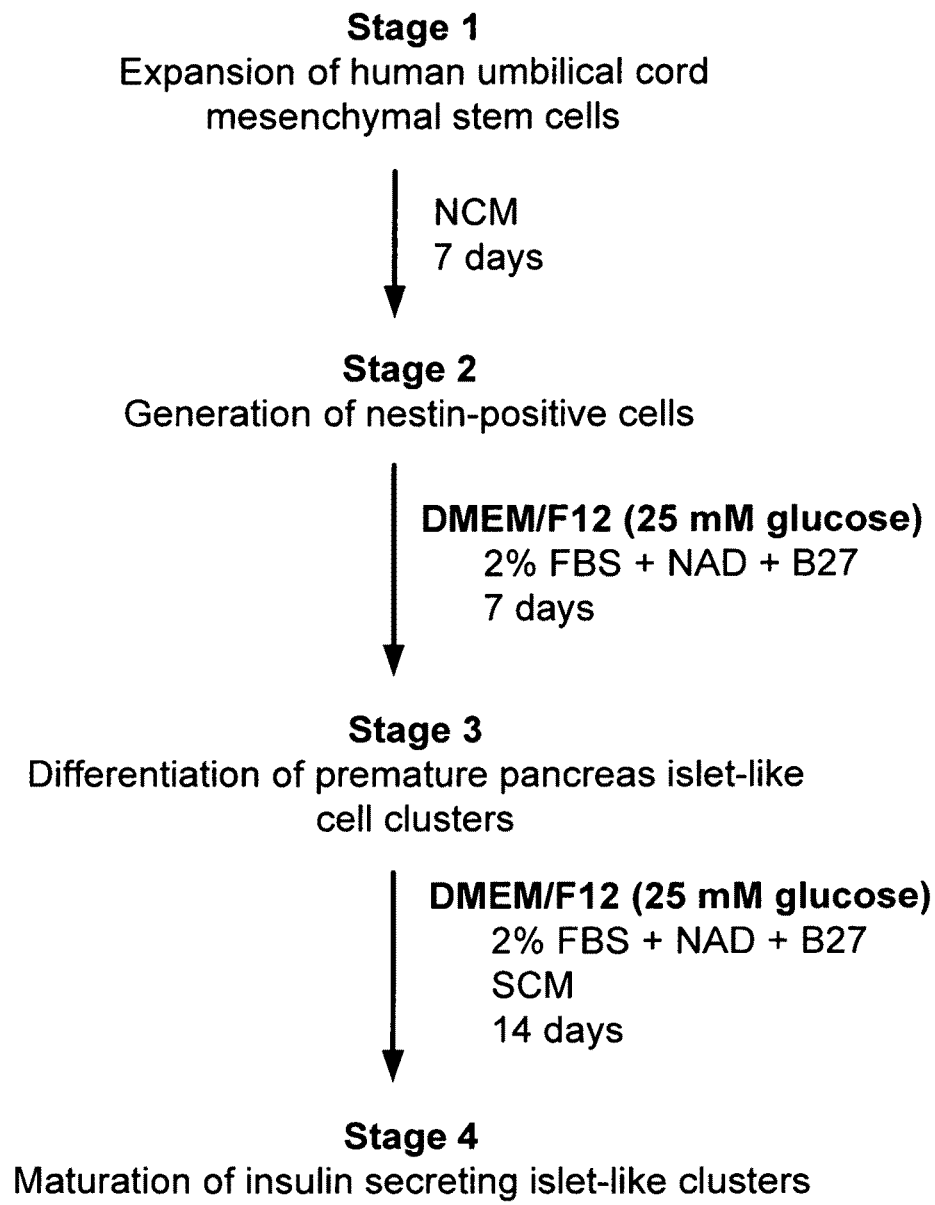
FIG. 4 shows the flow diagram for the inducement for transformation of HUMSCs into ICCs of the present invention.

As shown in FIG. 4, in order to culture and transform HUMSCs to ICCs ex viro, a stage-wise culture is performed. Firstly, the undifferentiated HUMSCs were cultured in DMEM medium with 10% fetal bovine serum for 3-6 days (stage 1); Next, HUMSCs were cultured in neuronal conditioned medium for 7 days, and the medium was changed everyday, in order to induce the formation of nestin-positive cells (stage 2); Then, the cells were suspended in DMEM/F12 medium with 2% fetal bovine serum (25 mM glucose), and 10 mM nicotinamide and vitamin B27 (Gibco, Cat. No. 17504-044) were added, and cultured for 7 days (stage 3); Finally, the differentiated ICCs were placed in stage 3 medium supplemented with SCM and cultured for 14 days (stage 4). If the stem cell conditioned medium is used to culture cells, it still can maintain the survival and activity of cells. It can be said that the culture by the stem cell medium has the similar effect with respect to the co-culture of HUMSCs. There were many ICCs generated. It was found that there were more glucagon and insulin expression of these ICCs through immunostaining method.

Figure 5:
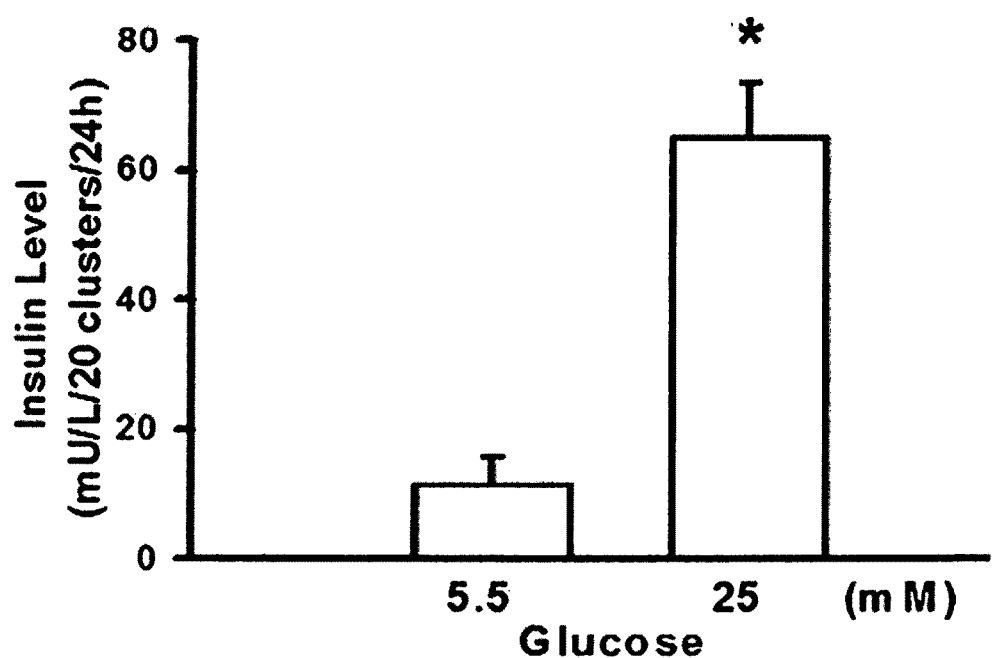
FIG. 5 shows the statistical diagram for the changes of insulin level induced by different concentration of glucose in the embodiment of the present invention.

In addition, in stage 3 medium, if the concentration of glucose was adjusted, it could found that the amount of insulin secreted by cell clusters was changed. For example, the cell clusters secreted lower levels of insulin on low glucose (5.5 mM) DMEM medium, but secreted higher levels of insulin on high glucose (25 mM) DMEM medium as shown in FIG. 5. This was similar to the physiological activity of normal pancreatic islet cells. It proved that ICCs transformed from the method of the invention still could maintain the function and activity of normal pancreatic islet cells.

Embodiment 6: Transplantation of ICCs

Seven days before the transplantation, the streptozotocin (STZ) was injected into the abdominal cavity of Sprague-Dawley rats to induce the diabetes. The injection dosage was 5 mg/kg/day, and it was continued for 2 day. Before the injection of streptozotocin, every week after the injection, and 3 days after the transplantation of cell clusters, take the blood from tail vein of rat, and use SURE-STEP blood glucose meter (Lifescan) to determine the concentration of blood glucose. One week after the rat was injected by streptozotocin, the concentration of blood glucose would be more than 400 mg/dl. 10% chloride hydrate was injected into the abdominal cavity of rats. After they were anaesthetized, the ICCs (about $2\times10^6$ cells) prepared in embodiment 5 were injected into the liver parenchyma of rat slowly through #22 syringe needle. As for the control group, the undifferentiated HUMSCs were transplanted to the liver of rat and only the physiological salt water was injected (false experimental group).

Figure 6A:
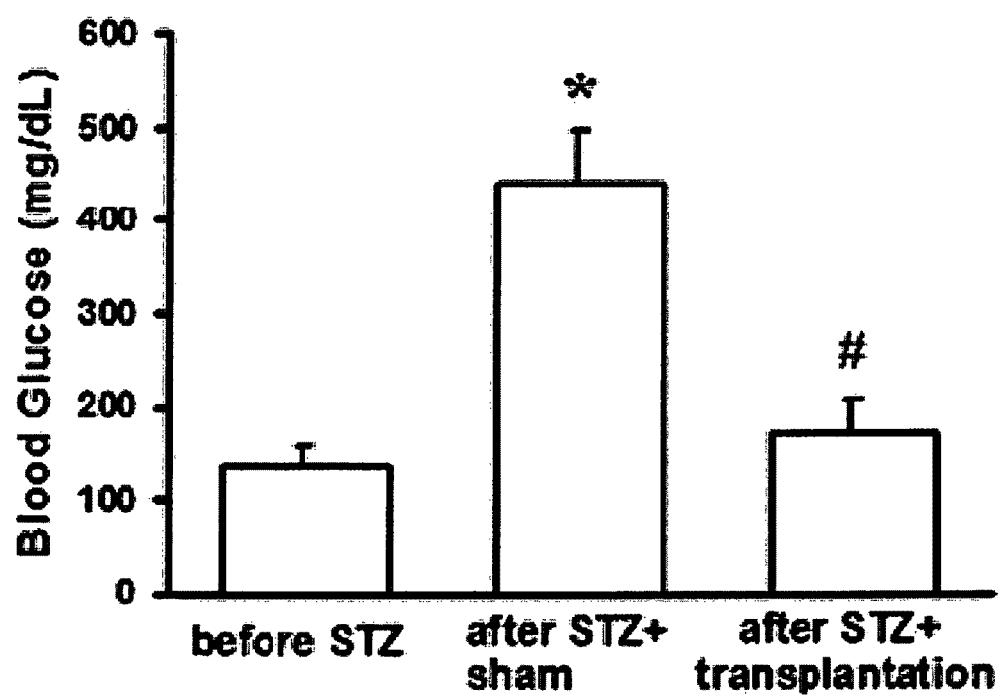
FIG. 6A, FIG. 6B, and FIG. 6C show the statistical diagram for the changes of blood glucose and serum human insulin levels in STZ-diabetic rats after clusters transplantation of the present invention.
Figure 6B:
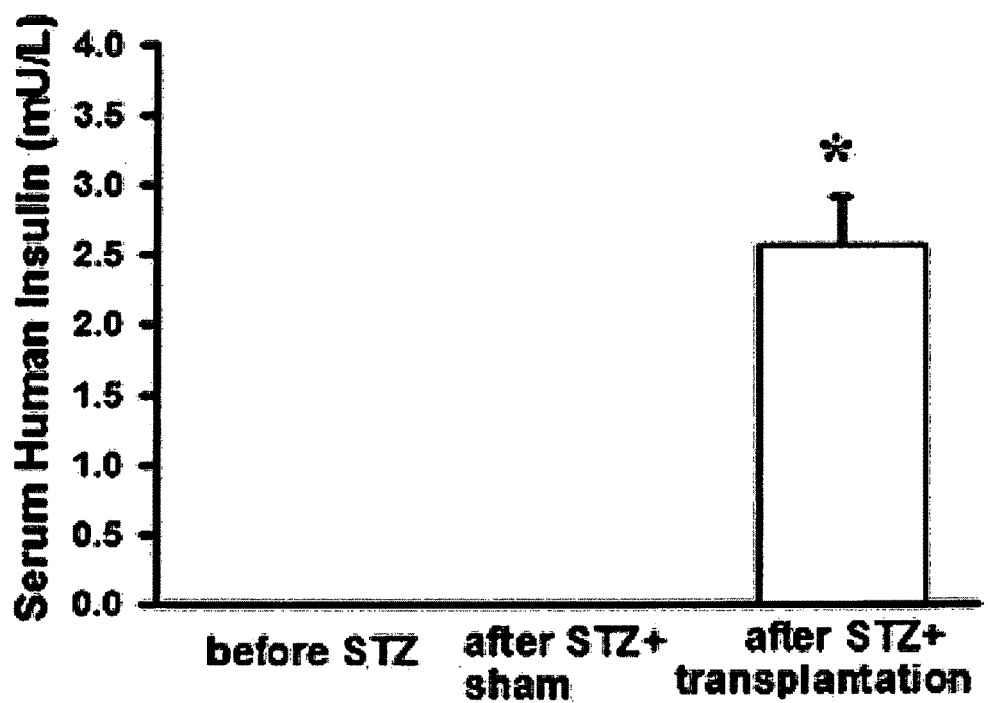
Figure 6C:
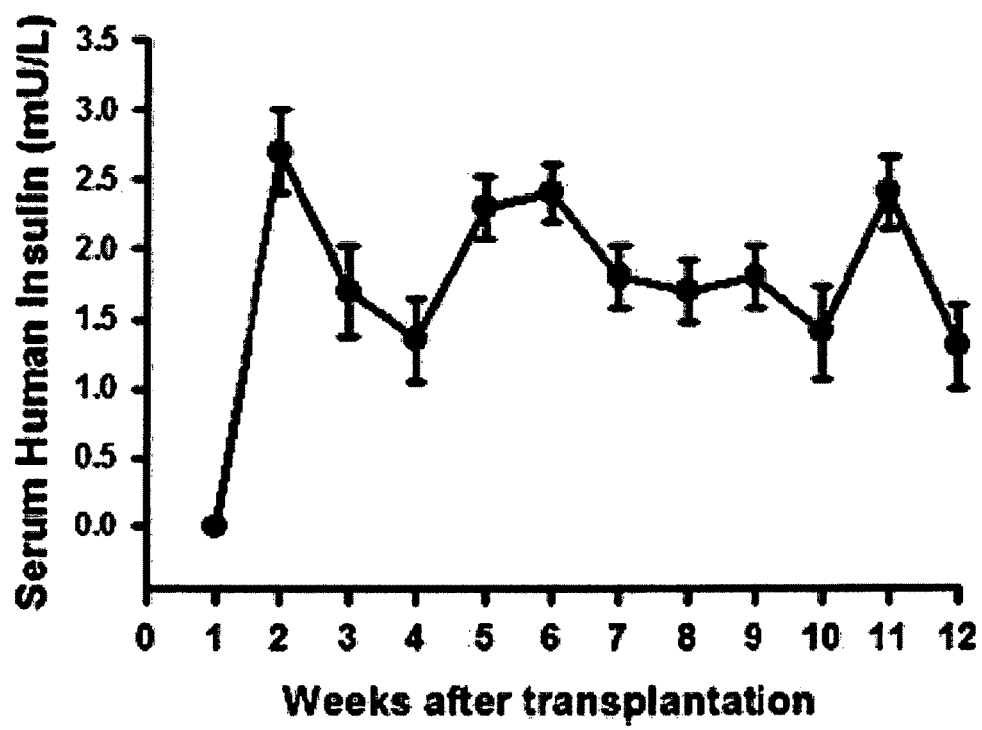

As the results shown in FIG. 6A, FIG. 6B and FIG. 6C after the ICCs prepared in embodiment 5 were transplanted to streptozotocin-induced diabetic rats, the concentration of blood glucose would be reduced, and the secretion of human insulin can be detected, which showed the ICCs induced and transformed according the method of the invention had the effect for inhibiting the diabetes.

Summarized by the above-mentioned description, according to the cell culture method of the present invention, the co-culture of HUMSCs or the stem cell medium can be used to culture, promote or maintain the survival and function of target cells, and promote or maintain renewing, repair and proliferative capabilities of target cells. In addition, according to the method of the present invention, HUMSCs can be induced to ICCs, which possesses similar function and activity of pancreatic islet cells.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A method to induce transformation of human islet cell cluster from human mesenchymal stem cells, comprising,
    (i) isolating human umbilical cord mesenchymal stem cells (HUMSCs) from human umbilical cord;
    (ii) culturing the isolated HUMSCs in a medium containing serum;
    (iii) culturing the cultured HUMSCs in mammalian neuronal cell conditioned medium (NCM) containing cytosine arabinoside (AraC) to produce nestin-positive cells;
    (iv) culturing the nestin-positive cells in DMEM/F12 medium containing 2% serum, nicotinamide (NAD) and vitamin B27 to produce islet-like cell clusters (ICCs); and
    (v) culturing the ICCs in DMEM/F12 medium containing 2% serum, NAD and vitamin B27 supplement with mesenchymal stem cell conditioned medium (SCM) containing one or more active components selected from the group consisting of interleukin-6 (IL-6), tissue inhibitor of metalloproteinase-1 (TIMP-1), tissue inhibitor of metalloproteinase-2 (TIMP-2), monocyte chemoattractant protein-1 (MCP-1), growth related oncogene (GRO), hepatocyte growth factor (HGF), insulin-like growth factor binding protein 4 (IGFBP-4) and interleukin-8 (IL-8) to produce ICCs expressing insulin and glucagon.

2. A cell culture method, comprising:
    (i) preparing a mammalian NCM; comprising
        (a) culturing mammalian brain cells in a single cell suspension in a medium comprising AraC, wherein AraC inhibits glial cells to produce mammalian NCM; and
        (b) harvest the medium;
    (ii) culture HUMSCs in mammalian NCM to produce nestin-positive cells;
    (iii) culture the nestin-positive cells in DMEM/F12 medium, glucose, insulin, NAD, and B27 to induce the nestin-positive cells to differentiate into premature ICCs;
    (iv) culture the premature ICCs in in DMEM/F12 medium, glucose, insulin, NAD, B27 and SCM, wherein SCM contains one or more active components selected from the group consisting of interleukin-6 (IL-6), tissue inhibitor of metalloproteinase-1 (TIMP-1), tissue inhibitor of metalloproteinase-2 (TIMP-2), monocyte chemoattractant protein-1 (MCP-1), growth related oncogene (GRO), hepatocyte growth factor (HGF), insulin-like growth factor binding protein 4 (IGFBP-4) and interleukin-8 (IL-8) to induce transformation of premature ICCs into mature insulin secreting ICCS.

3. A method of inducing transformation of human islet cluster from human mesenchymal stem cells comprising;
    (i) isolating HUMSCs;
    (ii) culturing the isolated HUMSCs in a medium containing serum;
    (iii) culturing the cultured HUMSCs from step (ii) in mammalian NCM containing AraC to produce nestin-positive cells; and
    (iv) culturing the nestin-positive cells in DMEM/F12 medium containing 2% serum, NAD and vitamin B27 to produce ICCs.

4. The method according to claim 3, wherein the neuronal conditioned medium is the cell medium for culturing mammalian brain cells.

5. The method according to claim 3, wherein the nestin positive cells are cultured in DMEM/F12 medium comprising glucose, insulin, NAD, and B27.

6. The method according to claim 2, wherein the concentration of glucose is 20 mM to 30 mM.

7. The method according to claim 2, wherein the concentration of glucose is 25 mM.

* * * * *